(12) United States Patent
Gebauer et al.

(10) Patent No.: US 8,377,296 B2
(45) Date of Patent: Feb. 19, 2013

(54) FILTER HOLDER IN A CHROMATOGRAPHY COLUMN

(75) Inventors: Klaus Gebauer, Uppsala (SE); Mircea Georgescu, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 0 days.

(21) Appl. No.: 13/319,816

(22) PCT Filed: May 10, 2010

(86) PCT No.: PCT/SE2010/050508
§ 371 (c)(1),
(2), (4) Date: Nov. 10, 2011

(87) PCT Pub. No.: WO2010/132011
PCT Pub. Date: Nov. 18, 2010

(65) Prior Publication Data
US 2012/0061306 A1 Mar. 15, 2012

(30) Foreign Application Priority Data
May 15, 2009 (SE) ...................................... 0900653

(51) Int. Cl.
*B01D 15/08* (2006.01)
(52) U.S. Cl. ........................ 210/198.2; 210/281; 210/656
(58) Field of Classification Search ................... 210/656, 210/659, 198.2, 281, 291, 456; 95/82, 85; 96/101, 103, 105
See application file for complete search history.

(56) References Cited

U.S. PATENT DOCUMENTS

| 4,710,289 A * | 12/1987 | Wermuth et al. | 210/198.2 |
|---|---|---|---|
| 5,169,522 A * | 12/1992 | Shalon et al. | 210/198.2 |
| 5,423,982 A * | 6/1995 | Jungbauer et al. | 210/198.2 |
| 5,462,659 A * | 10/1995 | Saxena et al. | 210/198.2 |
| 6,090,279 A * | 7/2000 | Davis et al. | 210/198.2 |
| 6,117,317 A * | 9/2000 | Dickson et al. | 210/198.2 |
| 6,123,849 A * | 9/2000 | Purdom | 210/656 |
| 6,139,732 A | 10/2000 | Pelletier | |
| 2003/0098280 A1 * | 5/2003 | Davis et al. | 210/656 |
| 2008/0017579 A1 * | 1/2008 | Hermansson et al. | 210/656 |

FOREIGN PATENT DOCUMENTS
WO   WO 2008/009412   1/2008

* cited by examiner

*Primary Examiner* — Ernest G Therkorn

(57) ABSTRACT

A filter holder to be used in a chromatography column is provided. Said filter holder comprising a filter squeezing part (356) facing the filter of the column essentially in the form of a plate and a squeezing means (354) adapted to squeeze the filter squeezing part (356) against the filter (204) to prevent any leakage of particulate medium from the bed space (209) of the column in between the filter holder and the filter (204). According to the invention said filter squeezing part (356) comprises at least one channel (338), providing fluid connections through the filter squeezing part (356) from the side of the filter squeezing part (356) facing the filter (204) and to the side of the filter squeezing part (356) facing the bed space (209).

5 Claims, 3 Drawing Sheets

FILTER HOLDER IN A CHROMATOGRAPHY COLUMN

CROSS-REFERENCE TO RELATED APPLICATIONS

This application is a filing under 35 U.S.C. §371 and claims priority to international patent application number PCT/SE2010/050508 filed May 10, 2010, published on Nov. 18, 2010 as WO 2010/132011, which claims priority to application number 0900653-7 filed in Sweden on May 15, 2009.

FIELD OF THE INVENTION

The present invention relates to chromatography columns. In particular, the invention relates to the fixation of particle retaining filters used for fluid distribution within columns.

BACKGROUND OF THE INVENTION

Chromatography is a well-established and valuable technique for separating chemical and biological substances and is widely used in research and industry, finding many applications in compound preparation, purification and analysis. There are many different forms of chromatography, liquid chromatography being of particular importance in the pharmaceutical and biological industries for the preparation, purification and analysis of proteins, peptides and nucleic acids.

A typical liquid chromatography apparatus has an upright housing in which a bed of packing material, which is usually particulate in nature and consists of a porous medium, rests against a permeable retaining layer. A liquid mobile phase enters through an inlet, for example at the top of the column, usually through a porous, perforated filter, mesh or frit, moves through the bed of packing material and is removed via an outlet, typically through a second filter, mesh or frit.

Columns used in liquid chromatography typically comprise a tubular body enclosing the porous chromatography medium through which the carrier liquid or mobile phase flows, with separation of substances or analytes taking place between the mobile phase and solid phase of the porous medium. Typically, the porous medium is enclosed in the column as a packed bed, generally formed by consolidating a suspension of discrete particles, known as slurry that is pumped, poured or sucked into the column, usually from a central bore or nozzle located at one end of the column. The production of a stable, even bed is critical to the final separation process and optimum results are found using bores which are centrally positioned through at least one column end piece.

Another critical feature in the separation of substances is the fluid distribution system, particularly as the cross-section of the chromatographic column increases. The efficiency of the chromatographic separation relies on the liquid distribution and collection system at the fluid inlet and outlet of the packed bed.

Ideally, the carrier liquid is uniformly introduced throughout the surface at the top of the packing, flows through the packing at the same velocity throughout the packing cross section, and is uniformly removed at the plane defined by the bottom of the packed bed.

Conventional distribution systems for use in liquid chromatography must address a number of inherent problems that have deleterious effects on the separation efficiency of the column. Among these problems is the non-uniform initial fluid distribution at the top of the packed bed. The problem of non-uniform initial fluid distribution refers generally to the problem of applying a sample volume simultaneously over the cross-sectional area of the packed bed. This problem will lead to increased dispersion in the chromatographic system by broadening the convective residence time distribution of a tracer substance transported with the fluid throughout the system. The dispersion generated by the liquid distribution system has to be controlled in relation to the amount of dispersion introduced by the chromatographic packed bed itself by means of diffusion and mixing effects. Without a simultaneous introduction of fluid in the plane defined by the top of the bed, it is virtually impossible to achieve so-called plug-flow behaviour, which is a uniform and well-defined movement of the sample through the packed bed and column, respectively, resulting in a uniform residence time distribution.

Standard fluid distribution systems consist of one central inlet for the mobile phase in combination with a thin distribution channel (gap) adjacent to the particle retaining filter (mesh, woven net or sinter) confining the top and bottom plane of the inlet and outlet of the packed bed. In theory and from experience it is known that such a system deteriorates in performance with increasing diameter of the column. This is due to the residence time difference between fluid elements travelling from the inlet to the outer column wall and those fluid elements which directly can enter the filter or net and the packed bed region below the inlet port. This difference in residence time is enlarged with column diameter and leads to chromatographic band broadening which becomes most severe with small particles. This problem corresponds to the non-uniform initial fluid distribution.

Non-uniform fluid distribution across the surface of the packed bed is also emanating from a reduction in the filter area in contact with the packed bed surface. For example, when providing a medium inlet, here also called a nozzle, for introducing the media into the column, which nozzle is protruding into the column centrally in one of the end units through the distribution system and the filter, the mobile phase can apparently not be added to the column exactly here as a central portion of the filter area is taken by the medium inlet. It is therefore desirable to reduce the size of this medium inlet as much as possible in order to maintain a large filter area and thereby minimizing the distortion in the flow pattern as much as possible. In practice, it is not only the size of the nozzle as such that causes a reduction in accessible area for fluid distribution across the packed bed, but also the sealing means around the nozzle. In order to avoid leakage of resin (particulate media) into the mobile phase a tight seal around the nozzle is required. Furthermore, sufficient mechanical support has to be provided such that the filter is kept in place around the nozzle. One way to do this is by welding the filter against a so-called nozzle retainer. However, welding is costly so other methods may be preferred. Another possibility is to provide a filter holder below the filter and around a part of the nozzle to prevent leakage. The filter holder comprises one squeezing means, here in the form of a cylindrical part which is for example a threaded cylinder adapted to surround the lowest part of the nozzle and one filter squeezing part for example in the form of a plate with a central hole adapted to receive the nozzle. Said filter squeezing part is attached to the cylindrical part such that the nozzle can pass through. The filter squeezing part is adapted to squeeze the filter against a corresponding element at the end piece of the column in order to prevent leakage of resin into the mobile phase in between the filter squeezing part and the filter. In order to get a reliable leak protection the area of the filter squeezing part needs to be a bit larger than a medium inlet passage provided in the filter for letting the medium inlet (nozzle) through. This will lead to a larger area in the column centreline blocking the liquid flow towards the packed bed and increasing the problem of non-uniform initial fluid distribution over the packed bed as described above.

For small columns this area of the filter squeezing part compared to the total cross section area of the column is relatively large and since no mobile phase will be applied beneath this filter holder area the mobile phase distribution is not optimal and the column efficiency will be reduced when operating the column. Furthermore, during sanitization of the packed bed it is important that the sanitization agents will reach the total volume of the packed bed efficiently which will be compromised when a large filter holder is blocking a too large area of the packed bed surface.

SUMMARY OF THE INVENTION

An object of the invention is to provide a filter holder which overcomes the drawbacks of the prior art systems.

This is achieved in a filter holder according to claim 1. The squeezing of the filter enables a cost efficient design, whereas the fluid connection channels applied to the filter holder allow a more uniform initial liquid distribution as liquid is distributed over a larger area of the packed bed surface. Furthermore, sanitization agents can be provided more efficiently over the column cross section area during column sanitization.

Embodiments of the invention are defined in the dependent claims.

DETAILED DESCRIPTION OF THE INVENTION

Figure 1:
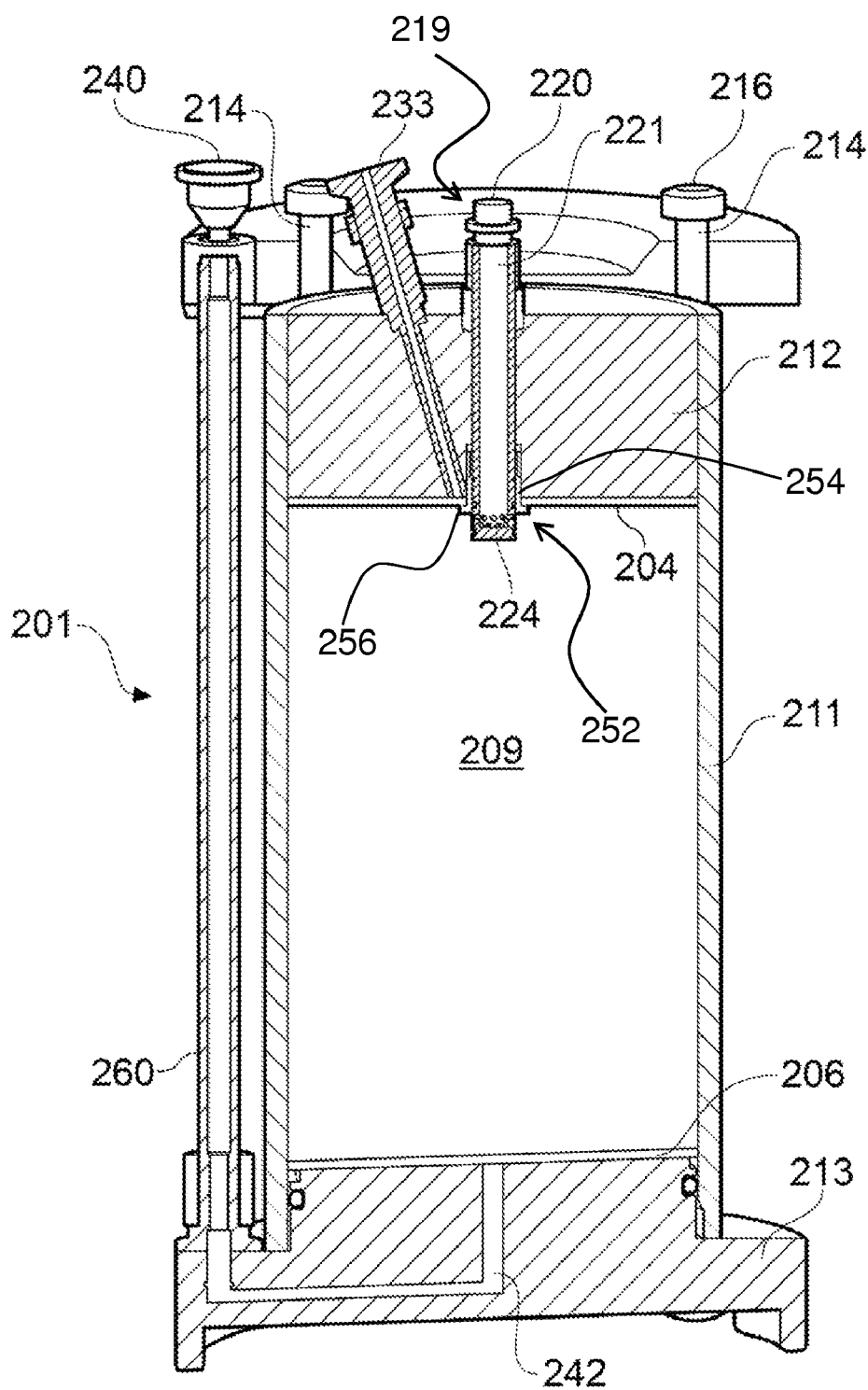
FIG. 1 is a three dimensional schematic showing a transverse sectional view of a chromatography column known from prior art.

A schematic cross-sectional view of a column known from prior art (see for example US20080017580) is shown in FIG. 1. The column 201 comprises a tubular housing 211, a first end unit 212 (partially shown) and a second end unit 213, secured together to form a fluid tight seal by means of tension rods 214 with heads 216. First filter 204 and second filter 206 are adjacent to the first end unit 212 and second end unit 213, respectively. These filters 204, 206, together with side wall 211, define a bed space 209 for containing a bed of particulate medium.

The housing 211 and end units 212, 213 are typically composed of stainless steel or a high-strength plastic material such as polypropylene. In a preferred embodiment, where the column is to be used for the separation of biologically active substances, the material is biologically inert such that it does not elicit an immune response in humans in accordance with United States Pharmacopia (USP) <88> class VI. Tension rods 214, with heads 216, secure the end units 212, 213 to the housing 211 to form a fluid-tight bed space 209 which is capable of withstanding high operating pressures.

The column can be packed with particulate medium in the form of a slurry through a medium inlet 219 in the form of a valve means 220, the valve means 220 comprising a central bore 221 and nozzle 224. In FIG. 1 the nozzle 224 is shown in its retracted position but it will be understood that it can be moved to a position within the bed space 209 to facilitate filling of the column (see FIG. 2). A wide range of nozzles can be used which facilitate the distribution and even packing of slurry within the bed space. One alternative for achieving an open/closed functionality at the packing valve and nozzle respectively is to have a nozzle that is fixed in the bed space (and thereby not retractable) and located adjacent to a movable element or sleeve on the inside or outside of the nozzle that opens and/or closes the nozzle depending on its position. Filters 204, 206 are each positioned on the interior face of the end units 212, 213 and act with the side wall 211 to define the bed space 209 and also to prevent leakage of particulate medium from the bed space 209. The medium inlet 219 passes through the first end unit 212 and through the first filter 204.

A distribution channel is suitably provided transversely across the face of the first end unit 212 and is in fluid communication with first filter 204. The fluid distribution channel acts to facilitate radial distribution of the liquid. Different types of distribution channels known from prior art can be applied.

Mobile phase or liquid containing one or more analytes or substances for separation on the column is added via first port 233. The liquid then passes through the first filter 204 into the bed space 209 that is packed with particulate medium (not shown). Chromatographic separation of analyte(s) which has been introduced onto the particulate medium in this manner is effected by introduction of, and elution by, mobile phase. The mobile phase will finally exit the column through second filter 206 and via passageway 242 to second port 240. The resulting fractions of mobile phase, which contain different analytes, can then be collected.

It will be understood by the skilled person that the column may be operated in either a "downflow" mode, as described above, or in an "upflow" mode where the direction of flow of the mobile phase is reversed such that it moves up the column. In upflow mode, mobile phase will enter the column via second port 240, move upwards through the bed of particulate medium, and exit the column and be collected via first port 233.

A filter holder 252 is provided below the first filter 204 and around a part of the medium inlet 219 to prevent leakage. The filter holder 252 comprises one squeezing means 254, here in the form of a cylindrical part 254 which suitably is a threaded cylinder adapted to surround the lowest (referred to orientation in FIG. 1) part of the medium inlet 219 and one filter squeezing part 256 which in this embodiment is in the form of a plate with a central hole adapted to receive the nozzle 224 of the medium inlet 219. Said filter squeezing part 256 needs to be essentially flat on the side facing the filter. However, the other side could for example be rounded instead of flat. Said filter squeezing part can be circular, square, pentagonal, hexagonal or have any number of sides. A non-circular form may be preferable to allow threading of the filter holder by use of a tool like a wrench, for example. Said filter squeezing part 256 is attached to the cylindrical part 254 such that the nozzle 224 can pass through. The squeezing means 254 is adapted to provide a force to the filter squeezing part 256 such that it is squeezed against the filter. In this embodiment this force is provided when the threaded cylinder is tightened. Hereby the filter squeezing part 256 squeezes the first filter 204 against the end unit 212 in order to prevent leakage of resin into the mobile phase in between the filter 204 and the filter holder. This filter squeezing part 256 needs to be of a certain diameter in order to be able to squeeze the filter 204 enough for preventing leakage. This means that the mobile phase or liquid that is being distributed throughout the area of the column by the distribution channel will not be distributed directly below this filter holder 252. Since the same seize of filter holders usually are used also for smaller columns the relative area where the mobile phase or liquid will not be distributed under the filter holder will be larger for smaller columns.

It will be understood that a wide range of column capacities is possible, typically ranging from 0.1 to 2000 litres. Preferred capacities when using the column as a disposable column are in the range of 0.1 to 50 litres.

Figure 2:
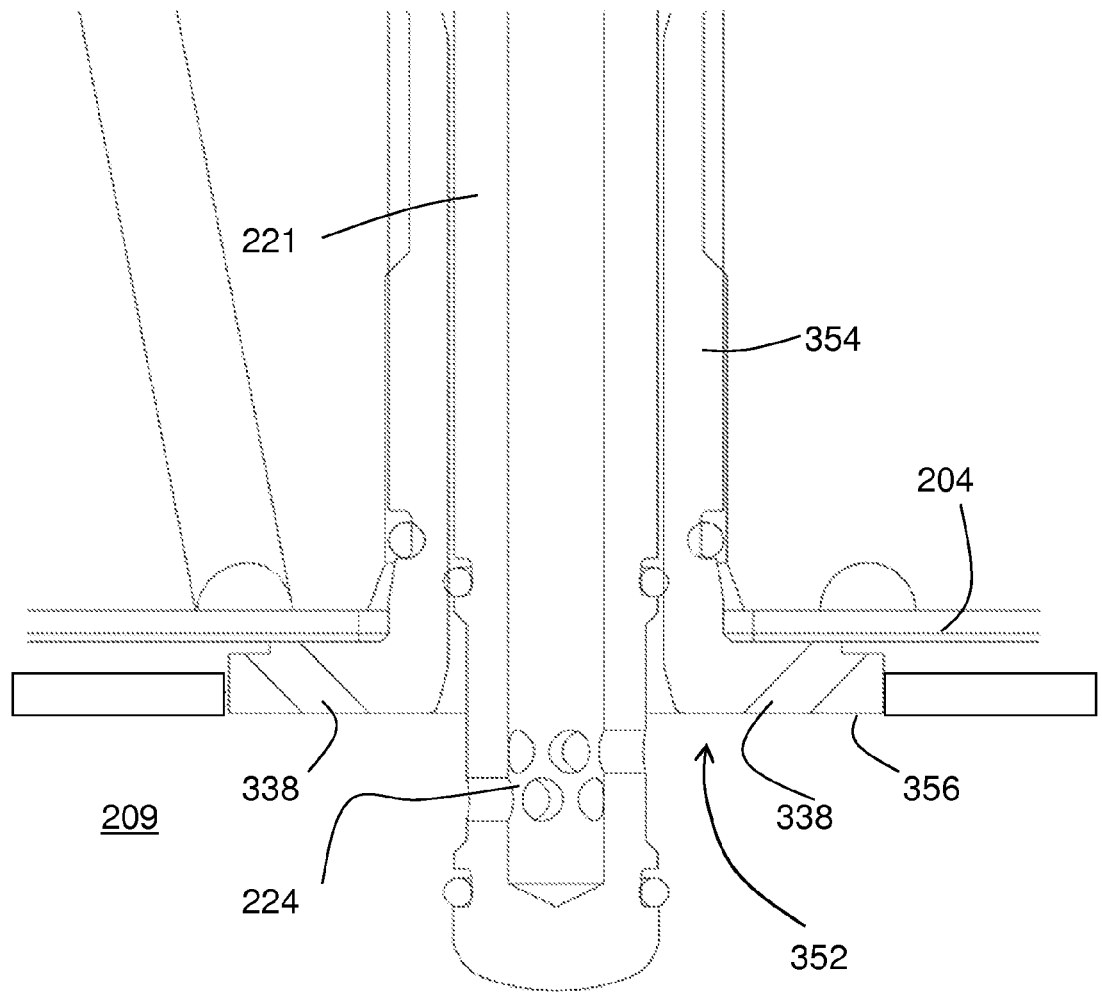
FIG. 2 is an enlarged schematic transverse sectional view of an end plate of a chromatography column comprising a filter holder according to the invention.

FIG. 2 is an enlarged transverse sectional view of the end plate of a chromatography column according to the invention. All the parts except from the filter holder are corresponding to the parts described with reference to FIG. 1 and the parts are numbered correspondingly. As can be seen, a nozzle 224 has been lowered into bed space 209 in order that the bed space 209 can be filled with particulate medium in the form of a slurry. It will be understood that the nozzle 224 will be retracted into the body of the central bore 221 once the column has been packed with the particulate medium and prior to any chromatographic separation on the column. A bed of packed particulate medium is obtained by conventional means well known in the art, for example by the movement of one of the end units to compress the bed.

A filter holder 352 comprising a squeezing means 354, here in the form of a threaded cylindrical part, and a filter squeezing part 356 is provided. According to the invention the filter squeezing part 356 comprises at least one, preferably multiple channels 338 that are in fluid contact with the first filter 204 and the bed space 209. In this Figure two channels 338 can be seen however any number of channels would be possible. Suitably, these channels 338 are according to the invention pointing inwardly, i.e. the openings on the side facing the interior of the column are closer to the centre of the column than the corresponding openings on the side facing the filter 204. Hereby the mobile phase is also distributed in the area and bed space directly below the filter holder. Hereby, the distribution of fluid across the bed space will be more uniform and the separation properties of the column will be better. In the embodiment shown in FIG. 2, media particles that enter the channels 338 from side of the bed space will be stopped by the filter 204. The inclination of the channels will provide liquid flow closer to the centre of the column and still providing a robust seal against particle leakage into the distribution channel.

Figure 3A:
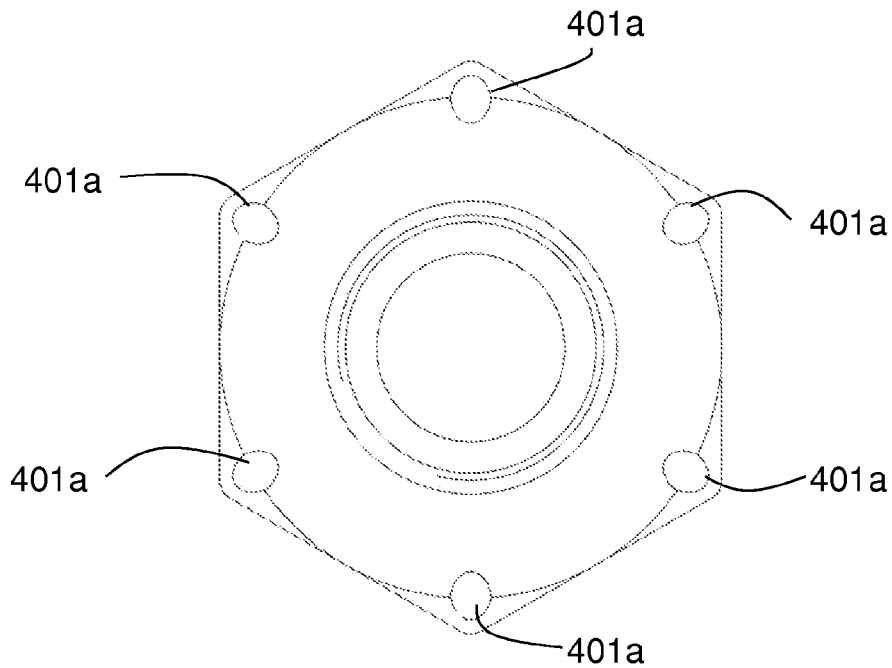
FIGS. 3a and 3b show a filter holder according to the invention schematically from two sides.
Figure 3B:
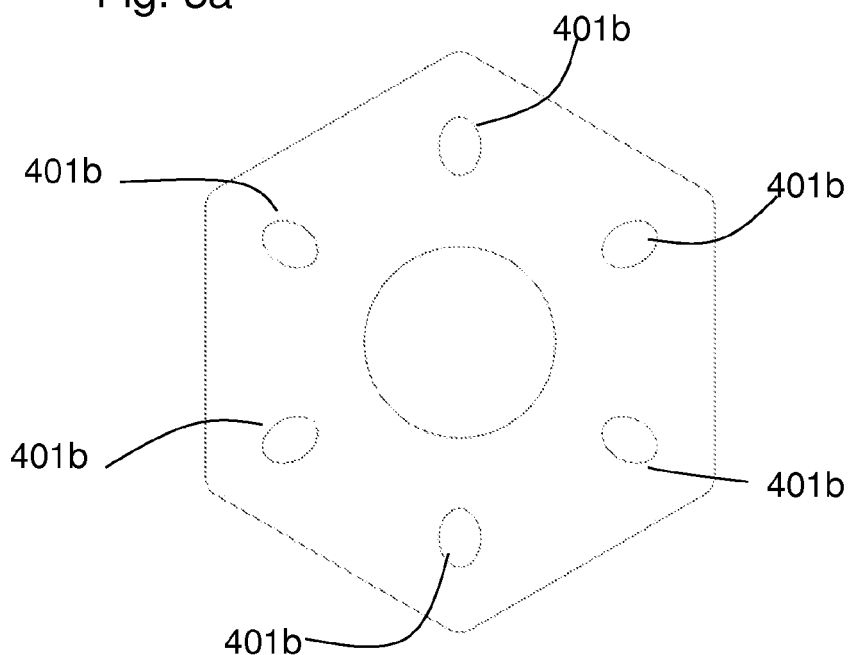

In FIG. 3a a filter holder according to one embodiment of the invention is shown as a separate component from above (i.e from the side of the filter holder that will be closest to the filter). In this embodiment 6 channels are provided. In this view first channel openings 401a can be seen. However the number of channels can be more or less than 6, but preferably at least 3. In FIG. 3b the same filter holder is shown from the bottom, i.e. from the side of the filter holder that will be facing the column interior. Here 6 second channel openings 401b are seen. Each one of the first channel openings 401a will of course be connected to one of the second channel openings 401b through a channel 338. It can be seen that these second channel openings 401b are closer to the centre of the filter holder than the first channel openings 401a due to the inclination of the channels 338 described above.

While preferred illustrative embodiments of the present invention are described, one skilled in the art will appreciate that the present invention can be practised by other than the described embodiments, which are presented for purposes of illustration only and not by way of limitation. The present invention is limited only by the claims that follow.

What is claimed is:

1. A filter holder to be used in a chromatography column, said chromatography column comprising a medium inlet (219) for providing particulate medium into the column, said medium inlet (219) entering an enclosed bed space (209) of the column through an end unit (212) of the column and through a first filter (204), said filter holder comprising:
   a filter squeezing part (356) adapted to be provided adjacent to the filter (204) on the side of the filter (204) facing the enclosed bed space (209), said filter squeezing part (356) facing the filter (204) essentially in the form of a plate with a central hole for receiving the medium inlet, and
   a squeezing means (354) adapted to squeeze the filter squeezing part (356) against the filter (204) to prevent any leakage of particulate medium from the bed space (209) in between the filter holder and the filter (204), wherein said filter squeezing part (356) comprises at least one channel (338), providing fluid connections through the filter squeezing part (356) from the side of the filter squeezing part (356) facing the filter (204) and to the side of the filter squeezing part (356) facing the bed space (209).

2. The filter holder of claim 1, wherein the channels (338) are inclined such that a second channel opening (401b) facing the bed space (209) is closer to the centre of the filter squeezing part (356) than a first channel opening (401a) facing the filter (204), said first channel opening (401a) being in fluid connection with the second channel opening (401b).

3. The filter holder of claim 1, wherein the number of channels (338) is at least three.

4. The filter holder of claim 1, wherein the squeezing means (354) is a threaded cylinder adapted to surround a part of the medium inlet (219).

5. A chromatography column comprising the filter holder of claim 1.

* * * * *